(12) United States Patent
Ambrosius et al.

(10) Patent No.: US 8,361,069 B2
(45) Date of Patent: Jan. 29, 2013

(54) ENERGIZED NEEDLES FOR WOUND SEALING

(75) Inventors: Kristel L. Ambrosius, Golden, CO (US); Paul R. Romero, Loveland, CO (US); Dylan R. Kingsley, Broomfield, CO (US); Randel A. Frazier, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 644 days.

(21) Appl. No.: 12/567,259

(22) Filed: Sep. 25, 2009

(65) Prior Publication Data

US 2011/0077647 A1 Mar. 31, 2011

(51) Int. Cl.
*A61B 18/18* (2006.01)
(52) U.S. Cl. .............................. 606/50; 606/213; 606/40
(58) Field of Classification Search .................. 606/40, 606/44, 50, 41, 51, 52, 213
See application file for complete search history.

(56) References Cited

U.S. PATENT DOCUMENTS

| | | | | |
|---|---|---|---|---|
| 4,535,772 A | * | 8/1985 | Sheehan | 606/218 |
| 5,665,085 A | * | 9/1997 | Nardella | 606/41 |
| 5,693,052 A | * | 12/1997 | Weaver | 606/51 |
| 5,797,927 A | | 8/1998 | Yoon | |
| 5,984,932 A | | 11/1999 | Yoon | |
| 5,984,939 A | | 11/1999 | Yoon | |
| 5,993,466 A | | 11/1999 | Yoon | |
| 5,993,467 A | | 11/1999 | Yoon | |
| 6,017,358 A | | 1/2000 | Yoon et al. | |
| 6,080,180 A | | 6/2000 | Yoon et al. | |
| 6,099,550 A | | 8/2000 | Yoon | |
| 6,123,701 A | * | 9/2000 | Nezhat | 606/33 |
| 6,162,220 A | * | 12/2000 | Nezhat | 606/48 |
| 6,165,169 A | | 12/2000 | Panescu et al. | |
| 6,190,386 B1 | * | 2/2001 | Rydell | 606/51 |
| 6,261,307 B1 | | 7/2001 | Yoon et al. | |

(Continued)

FOREIGN PATENT DOCUMENTS

| | | |
|---|---|---|
| EP | 0 537 570 B1 | 4/1993 |
| EP | 0 647 431 B1 | 4/1995 |

(Continued)

OTHER PUBLICATIONS

European Search Report dated Apr. 17, 2007 for Corresponding Patent Application EP06026840.

(Continued)

*Primary Examiner* — Linda Dvorak
*Assistant Examiner* — Jocelyn D Ram

(57) ABSTRACT

A bipolar electrosurgical instrument has a first and a second set of needle like structures. Each set of needle like structures is functional for puncturing the skin of a patient on opposing sides of a wound or cut. Each needle comprises a body and a pointed portion at a distal end. The distal end is structured to form a sealing surface with an opposing needle on a needle of the other set. The sealing surfaces are adapted to connect to an electrical energy source such that the sealing surfaces are capable of conducting bipolar energy therebetween. The first and second set of needle like structures are movable from a first position where the needles are disposed in spaced relation relative to one another to a second position where the first and second sets of needles members are closer to one another. A mechanical force applied to or within a housing is utilized to move the needles sets from the first position to the second position.

4 Claims, 14 Drawing Sheets

U.S. PATENT DOCUMENTS

| | | | |
|---|---|---|---|
| 6,277,116 B1 * | 8/2001 | Utely et al. | 606/42 |
| 6,346,104 B2 | 2/2002 | Daly et al. | |
| 6,436,097 B1 | 8/2002 | Nardella | |
| 6,620,156 B1 * | 9/2003 | Garito et al. | 606/32 |
| 6,656,177 B2 | 12/2003 | Truckai et al. | |
| 6,723,092 B2 * | 4/2004 | Brown et al. | 606/41 |
| 6,881,213 B2 * | 4/2005 | Ryan et al. | 606/41 |
| 6,979,328 B2 | 12/2005 | Baerveldt et al. | |
| 7,217,269 B2 | 5/2007 | El-Galley et al. | |
| 2002/0165541 A1 | 11/2002 | Whitman | |
| 2003/0114845 A1 * | 6/2003 | Paton et al. | 606/40 |
| 2003/0114851 A1 | 6/2003 | Truckai et al. | |
| 2003/0236518 A1 | 12/2003 | Marchitto et al. | |
| 2004/0210282 A1 | 10/2004 | Flock et al. | |
| 2005/0070896 A1 * | 3/2005 | Daniel et al. | 606/50 |
| 2005/0072827 A1 | 4/2005 | Mollenauer | |
| 2005/0131390 A1 | 6/2005 | Heinrich et al. | |
| 2007/0118115 A1 * | 5/2007 | Artale et al. | 606/51 |
| 2007/0213705 A1 * | 9/2007 | Schmid | 606/44 |
| 2008/0125775 A1 * | 5/2008 | Morris | 606/50 |

FOREIGN PATENT DOCUMENTS

| | | |
|---|---|---|
| EP | 0 738 501 A1 | 10/1996 |
| EP | 1 813 203 A | 8/2007 |
| WO | WO 96/05776 | 2/1996 |
| WO | WO 97/00646 | 1/1997 |
| WO | WO 97/29694 | 8/1997 |
| WO | WO 97/40760 A1 | 11/1997 |
| WO | WO 99/03407 | 1/1999 |
| WO | WO 99/52489 A1 | 10/1999 |
| WO | WO 00/41638 | 7/2000 |
| WO | WO 03/030743 A2 | 10/2002 |
| WO | WO 03/090630 A2 | 11/2003 |
| WO | WO 2004/032760 A2 | 4/2004 |
| WO | WO 2007/030753 A2 | 3/2007 |
| WO | WO 2007/118179 A2 | 10/2007 |

OTHER PUBLICATIONS

International Search Report for corresponding PCT Application—PCT/US06/21524—Date of Mailing May 28, 2008 (4 Pages).

Detemple, P., "Microtechnology in Modern Health Care", *Med Device Technol.* 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for corresponding EP 08252703.7 dated Oct. 31, 2008 (7 pages).

* cited by examiner

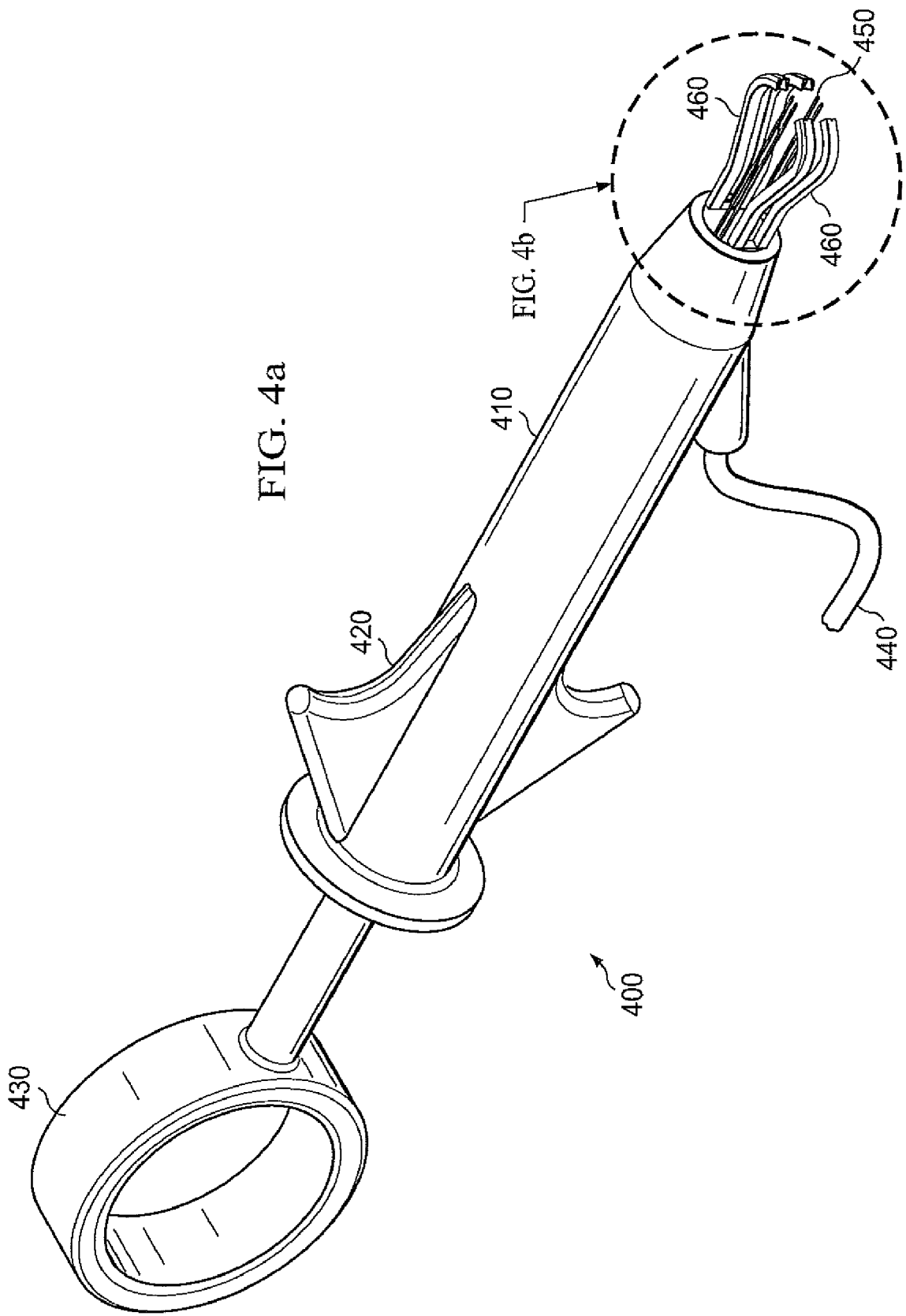

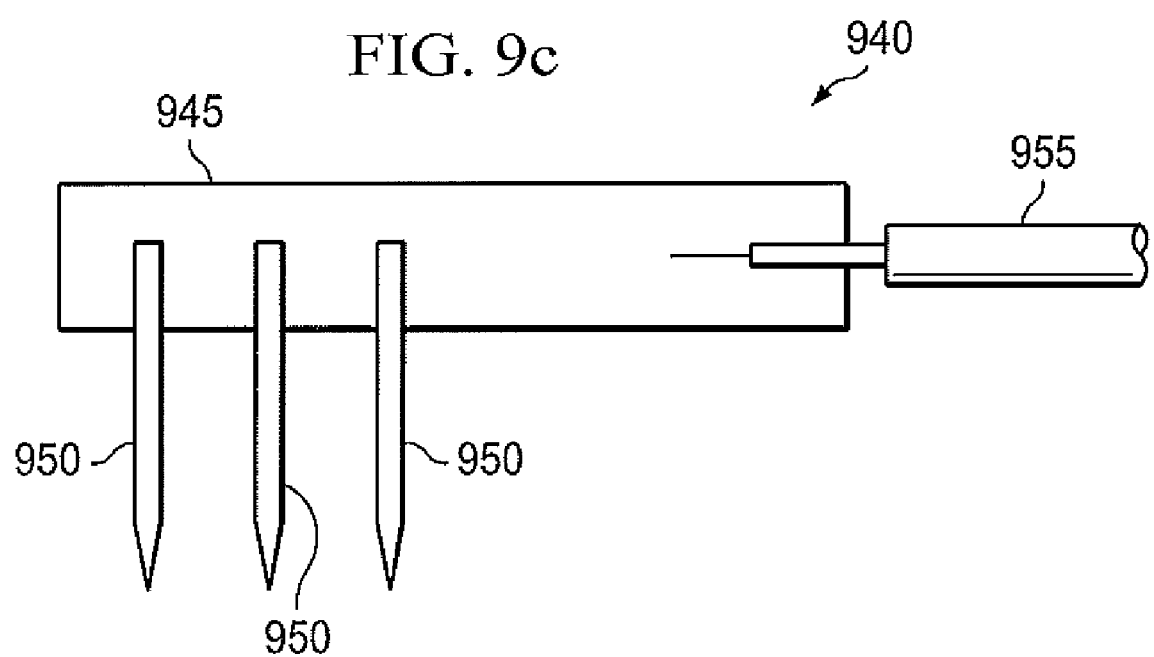
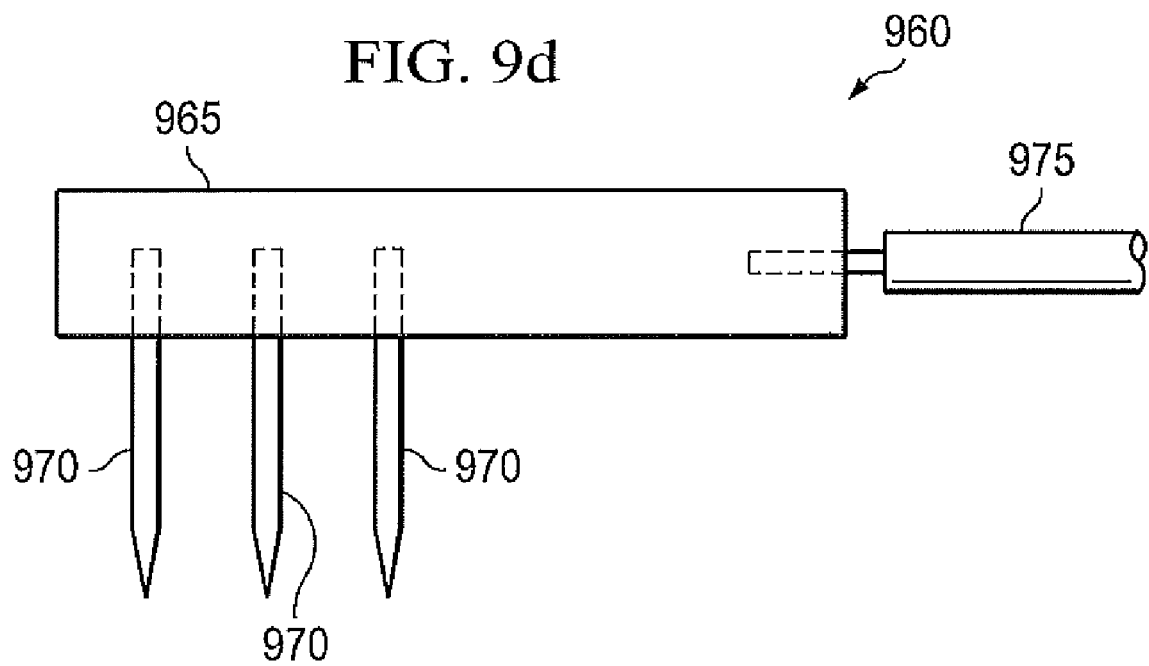

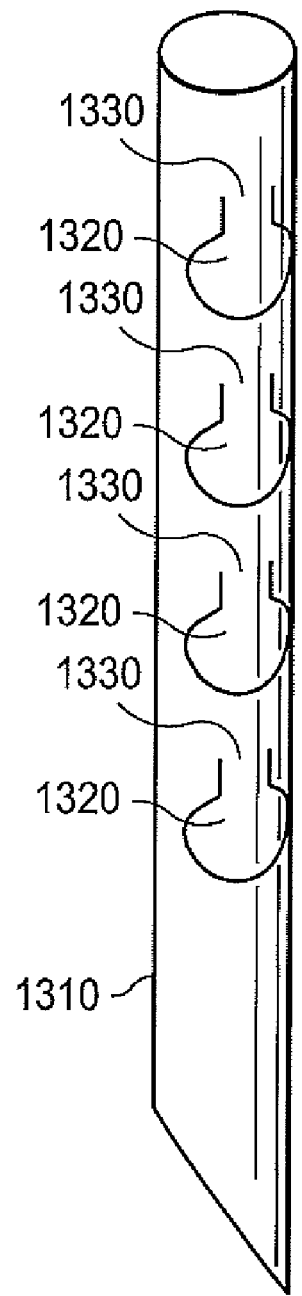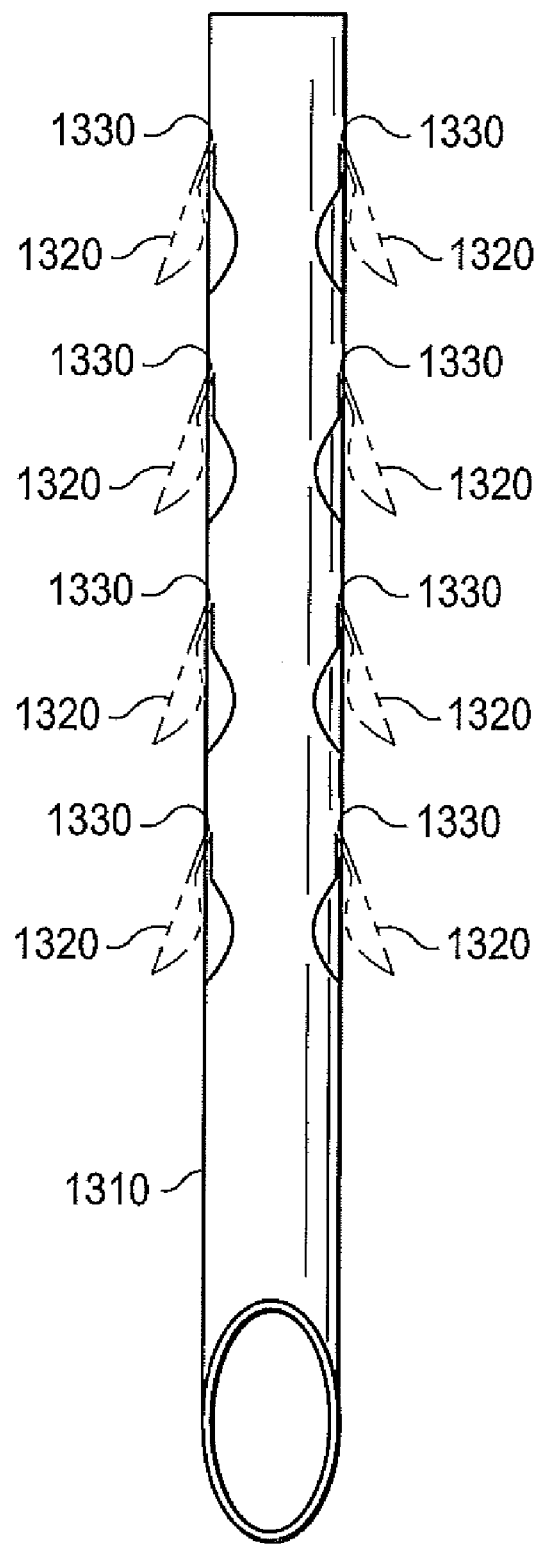
FIG. 13a
FIG. 13b

ENERGIZED NEEDLES FOR WOUND SEALING

BACKGROUND

The present disclosure relates to an electrosurgical instrument for closing epidermis or body tissue sections in a human or animal and, more particularly, to a bipolar electrosurgical instrument for energizing needles for wound sealing.

There are six main purposes of wound and, particularly, skin closure: 1) the elimination of dead space where infection or hematoma can occur, 2) realigning tissues correctly to reduce remodeling, 3) to hold aligned tissue together utilizing the correct tension until healing has occurred, 4) to avoid the introduction of infection, 5) to enhance cosmetic results, and 6) to speed up the ability of the patient to return to normal activity. In order to accomplish these goals, a number of techniques are currently in common use. These include sutures, staples, tissue adhesives, adhesive skin closure strips and hair ties. Each of these methods has their disadvantages.

Sutures are the oldest and still the most common method of wound closure. This method has some advantages that are worth noting. Any mistakes can be easily rectified, all types of wounds (deep or superficial) can be closed with sutures, and they are mechanically strong (12 times stronger than wounds closed with tissue adhesives). However, there are disadvantages as well. Suturing is time consuming and requires a good amount of skill. Strict aseptic techniques must be maintained to avoid contamination of the wound—tissue must be tied together with the appropriate tensile strength (too loose can cause tissue to not heal, too tight can damage the tissue), additional damage caused by the needle, and suturing does not provide complete homeostasis.

Staples are the second most popular method of skin closure. Staples and sutures are very similar in patient comfort as well as cosmetic results. Stapling, however, is the fastest method of skin closure, has the lowest level of tissue reactivity, less chance of infection, and does not require a local anesthetic. However, staples are often more expensive than sutures and can only be used to close superficial skin layers, require a follow up visit to remove the staples and it can be difficult to properly align the tissue, thus increasing the chance of scar deformity.

Tissue adhesives have been around for approximately 60 years and are starting to become more popular. While they are substantially more expensive that sutures or staples, they can break under high tensile force and are not particularly useful for areas that will be washed frequently. Advantageously, gluing wounds together is a relatively easy skill to perfect. Glue provides a waterproof seal, is quicker than suturing and anesthetics generally are not needed.

Adhesive skin closure strips are available in normal, reinforced or elasticized form. These strips come in predetermined lengths or they can come in rolls and be cut down to the appropriate size. These strips have the advantages of being easy to use, reduce the risk of infection, reduce the need for anesthetic, can be used in conjunction with either sutures or staples to enhance mechanical strength, are comfortable and produce good cosmetic results. However, adhesive skin closure strips have the disadvantage that they do not adhere well to sweaty, oily or hairy areas. They also cannot be used on deep wounds without the reinforcement of sutures. Further, they are complex to use when the wound is not straight, and they are generally unsuitable for use over joints.

The zipper is a fairly newly introduced method of skin sealing. The zipper is applied with an adhesive strip to both sides of a wound and then closed. The zipper can be rapidly applied without anesthetic and give good aesthetic results. Advantageously, the zipper is substantially less costly than staples or suture kits and can also reduce the chance of infection. However, the zipper can detach if it becomes too dirty. It also cannot be used on wounds that have more than a 20 degree curvature, and can only be used for deeper wounds without sutures.

The hair apposition technique is applicable to scalp wounds. In this technique, hair is taken from both sides of a scalp wound and tied across the wound to achieve tissue apposition. The knot can then be secured with benzoic tincture, tissue adhesives or adhesive sprays. This method can only be used with hair that is approximately 3 cm long or longer. Additionally, the technique can only be used on superficial wounds.

SUMMARY OF THE INVENTION

According to one embodiment of the present invention, there is provided an apparatus which utilizes the advantages of needles, or needle-like structures, puncturing and penetrating into the skin of a patient with minimal damage. Two opposing needles provide the basis for a bipolar sealing device. One needle, or set of needles, is inserted into the skin of a patient on each side of a wound. The two sets of needles are brought together mechanically. The needles are energized electrically and a seal of the dermis and sub-dermal layers is created. The depth and width of the resulting seal is adjustable with needle size and placement.

Multiple needle sets provide increased stability and practicality depending on the size of the wound and the mechanical force required to close a particular wound. There can be anywhere from 2 to 100, or more, needles per set. However, there is no functional limit to the number of needles per set.

In one embodiment of the invention, energy required to seal a wound is focused. This is accomplished by using an insulator to hold the needles. The seal plate surface, which incorporates the puncture tip, is a metallic or other conductor. The invention is functional with current medical generators with modifications to the mathematical algorithms used to control current flow.

BRIEF DESCRIPTION OF THE DRAWINGS

FIG. 4a is a view of an embodiment of the invention showing a set of opposing needle sets and a housing and actuation mechanism.

FIG. 4b is a view of an embodiment of the invention showing an exploded portion of the embodiment of FIG. 4a.

FIGS. 9a-9d are embodiments of needle holders.

FIG. 13 is an embodiment of a needle configuration.

DETAILED DESCRIPTION OF THE EMBODIMENTS

In one embodiment of the invention, a first set of needles is opposed by a second set of needles. The needles are capable of puncturing the skin of a patient. A mechanical force is used to squeeze the needles together. An electrical current is used to energize the needles and a seal of the dermis and sub-dermal layers of the skin is created.

Figure 1:
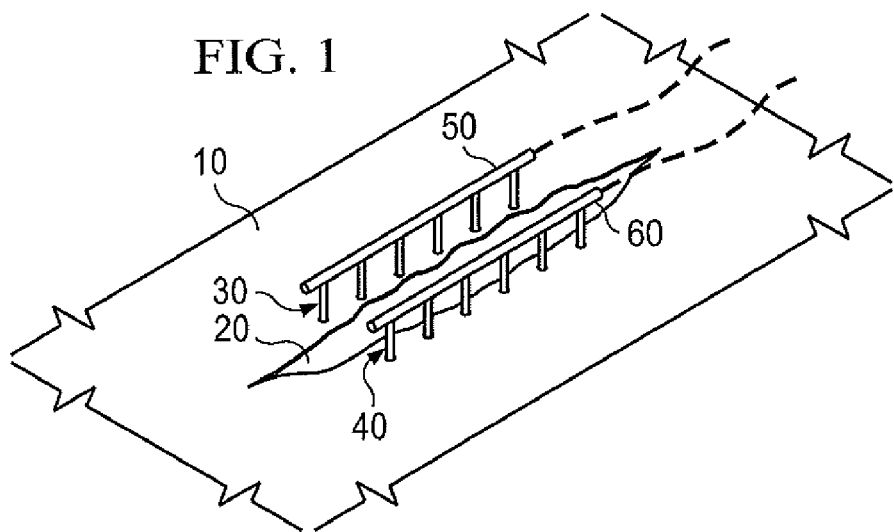
FIG. 1 is a view of a bipolar set of energized needles for wound sealing, according to one embodiment of the invention.

FIG. 1 is a perspective view of an embodiment of the invention being used to seal a wound. A portion of a patient 10 is shown. The portion shown is any portion of a patient that is capable of accepting a wound or cut. The portion 10 has received a wound 20. A first set of needles 30 is shown on one side of the wound 20. A second set of needles 40 is shown opposite the first set of needles 30. Connecting the first and second set of needles is a first connector 50 and second connector 60, respectively. The connectors 50, 60 provide a point of connection for the needles in the first 30 and second 40 sets. One skilled in the art will understand that there are many techniques available for connecting the needles in each set 30, 40 so that they are able to be energized. For instance, each needle set is connected with a metal bar that runs from the distal end of each set of needles 30, 40 to the proximal end of the needles 30, 40. The bar connecting the needles on each side is wired to a suitable energy source (not shown).

The term "needle" is not limited to the present embodiment or depiction. Naturally, the efficacy of the present invention may be optimized by different types of penetrating structures, such as tines, spikes or other structure capable of puncturing, or penetrating, the skin of a patient on opposing sides of a wound and drawing the wound together when receiving a mechanical, or electromechanical, force. The term "needle" is used to include any device, mechanism or structure capable of puncturing and gripping the skin of a patient.

Generally, skin is composed of three outer layers. Outermost is an epidermis, second most outermost is a dermis and third outermost is a subcutaneous adipose portion. Full depth skin incisions usually involve a laceration or injury where a tissue section having such an epidermis, dermis and subcutaneous portion are all possibly cut.

Still referring to FIG. 1, the first 30 and second 40 set of needles penetrate the skin. The depth of penetration is sufficient to hold the needles in place in the skin as the needle sets 30, 40 are drawn together by a suitable force. As discussed above, the length and gauge of the needles is predetermined for optimal depth during insertion. A predetermined optimal amount of tissue is gripped by the needles. Alternatively, depth of insertion can be determined by experienced judgment of trained medical personnel.

A mechanical force is applied to the needle sets 30, 40 that squeezes the two sets 30, 40 together. Each needle of the sets 30, 40 includes a sealing surface (shown in FIGS. 3a and 3b). The two needle sets 30, 40 clamp together due to the applied force tightly on the skin, allowing each needle pair to form an active seal site. Energy is applied to the needle sets 30, 40 via the connectors 50, 60. The connectors 50, 60 are connected to a suitable energy generator (not shown).

Figure 2:
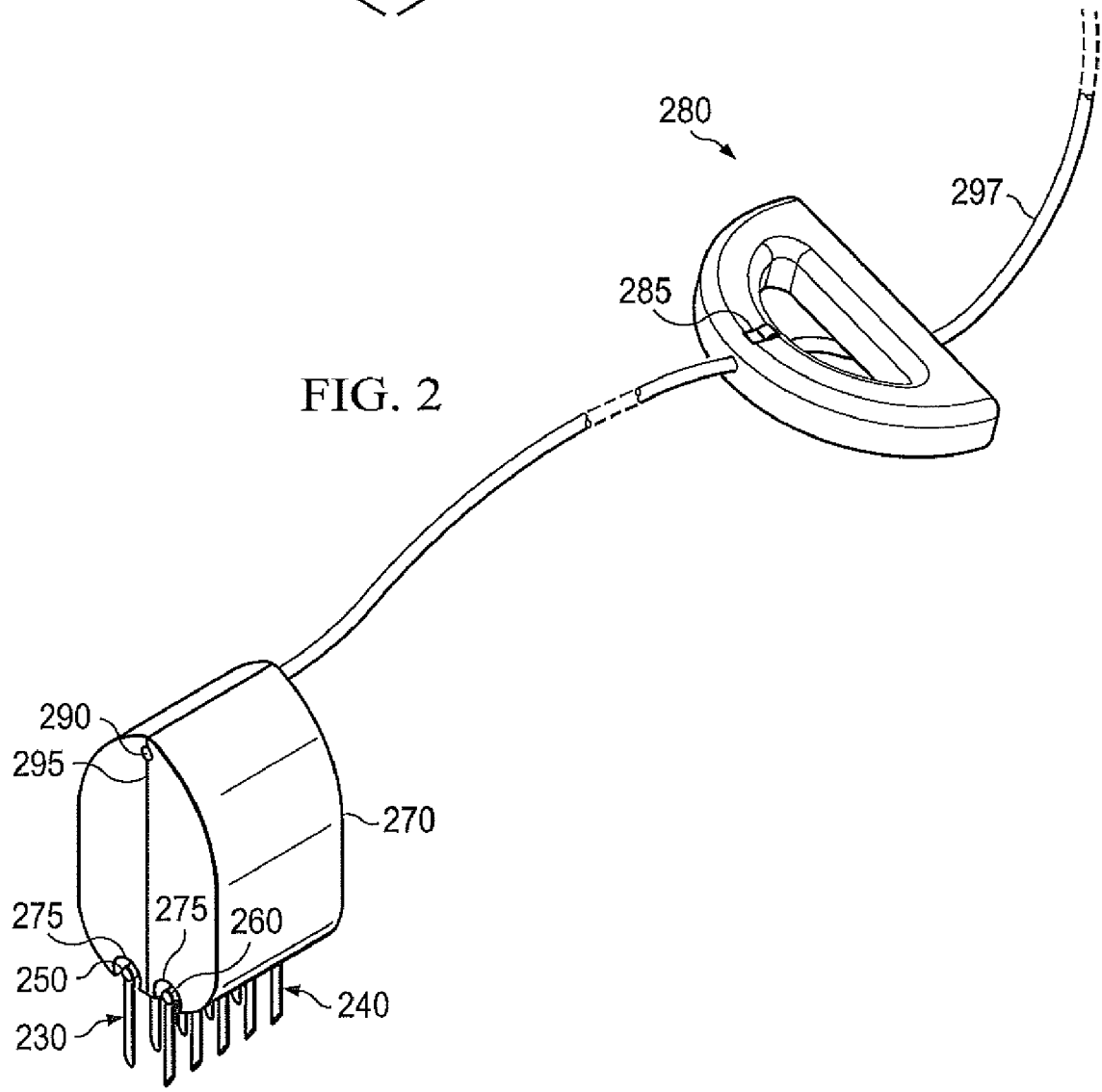
FIG. 2 is a view of an embodiment of the invention showing a mechanical clamping mechanism.

FIG. 2 is an embodiment of the invention showing a mechanism for applying a force to the opposing needle sets. A first set of needles 230 is attached to a first connector 250. A second set of needles 240 is attached to a second connector 260. The first 250 and second 260 connectors are embedded in a housing unit 270. The housing unit 270 has a pair of adaptations 275 in the form of grooves designed to hold the first 250 and second 260 connectors. The housing unit 270 is attached to an actuator 280. The actuation mechanism 280 allows for user manipulation of the housing unit 270. User interaction is also operable for applying electrical energy to the needle sets 230, 240 via the connectors 250, 260. The energy can be switched on or off using a control 285.

In the embodiment shown in FIG. 2, the housing unit 270 applies a mechanical force to the needle sets 230, 240 via a manual application. A direct pressure is applied to the housing 270 by a user. The housing hinges at hinge 290 and opening 295 allows the housing 270 to open and close. Accordingly, the housing unit 270 effects a mechanical force substantial enough to draw the first 250 and second 260 connectors, and first 230 and second 240 needle sets, toward each other.

The actuation mechanism 280 in the current embodiment provides a mechanical engagement of the housing unit 270. The mechanical engagement provides a range of force. Those skilled in the art understand the variety of suitable mechanisms available for applying a mechanical force.

Continuing to refer to FIG. 2, the actuation mechanism 280 connects to a suitable generator (not shown). The generator unit may be a standard type generator, such as that used with the LigaSure™ electrosurgical instruments available from Covidien (formerly Valleylab). The generator provides an energy source for the first 230 and second 240 needle sets. Alternatively, the generator may be a custom unit designed to specifically provide power to the needles of the invention. Those skilled in the art understand the energy type associated with the generator may be radiofrequency, microwave, laser or other suitable type.

The generator provides energy to the needle sets 230, 240, which allows the needles to heat. The heated needles 230, 240 seal the dermis and sub-dermal layers of a wound.

Figure 3A:
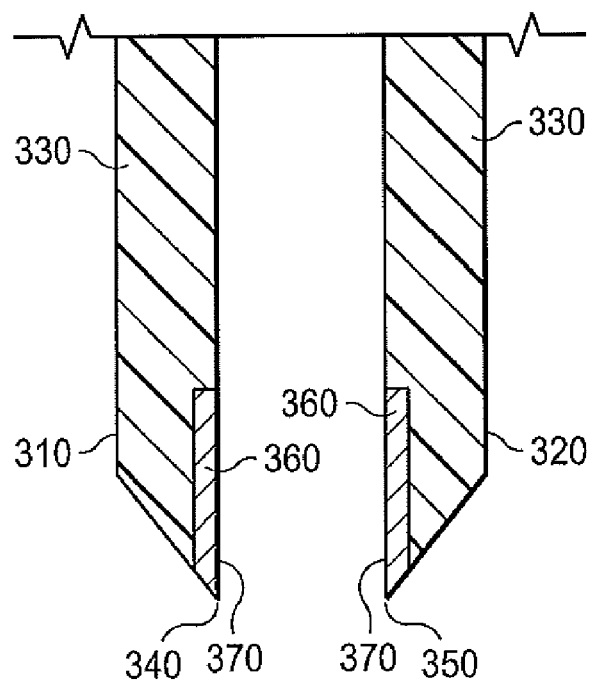
FIG. 3a is a view of an embodiment of an individual needle pair in an open position.

FIG. 3a shows a pair of opposing needles of the invention. A first needle 310 is opposed by a second needle 320. It is understood that a plurality of needles 310, 320 may be opposed to each other. FIG. 3a is limited to showing a single pair of opposing needles. Each needle of the opposing needles 310, 320 has a needle body 330. The needle body 330 extends downward from a connector (not shown) which connects the plurality of needles together electrically. First needle 310 has a pointed end 340. Second needle 320 has a pointed end 350. The pointed ends 340, 350 increase the ability of the needles to puncture at least the epidermis and potentially the dermis and subcutaneous layers of a patient's skin.

Toward the portion of the needles 310, 320 having the pointed end, there is an electrical conducting material 360. In an embodiment of the invention, the electrical conducting material 360 forms the points 340, 350. The electrical conducting material 360 on each of the needles 310, 320 forms a flat surface 370 on the inner side of the needles at the distal end of the needles 310, 320. The surface 370 can be any suitable shape. By distal end it is understood to be that end of the device that is furthest from a user, the user applying inputs either at the housing unit (not shown in FIG. 3) or at the actuation mechanism (not shown in FIG. 3). The flat surfaces on the inner portions of the distal ends of the needles 310, 320 form a sealing surface when the needles 310, 320 come together upon application of a suitable force.

The electrical conducting material 360 of each of the needles 310, 320 is connected electrically to a generator (not shown). The generator provides an electrical energy through a connection to the electrical conducting material 360. The connection may be a wire or other suitable conductive path that runs through the body 330 of the needles 310, 320.

In order to maintain a sound electrical connection, the body 330 of the needles 310, 320 are comprised of an electrical insulator. There are many different acceptable electrical insulators available. Acceptable insulators include plastic, ceramic or glass.

In an embodiment, a plastic tip needle and a metal seal surface provides electrical isolation to all areas other than the intended seal area. This isolation minimizes thermal spread near the seal area. Fabrication of the needle in an embodiment is by over-molding a single metal piece containing the metal seal surface for all of the needles and electrically connecting all of the seal surfaces. Alternatively, each needle is a separate piece.

In an alternative embodiment, a metal needle is coated with a non-conductive material. A seal surface area is masked from the coating. Alternatively, the coating is etched away to expose the metal seal surface.

Figure 3B:
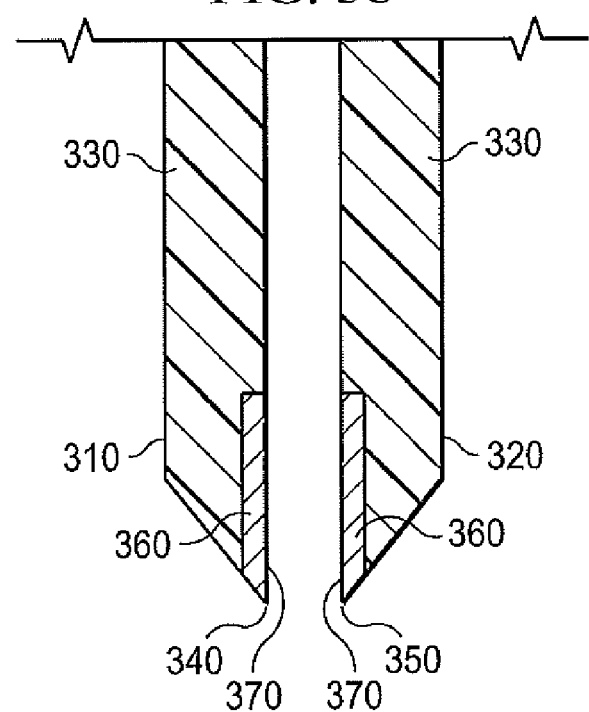
FIG. 3b is a view of an embodiment of an individual needle pair in a closed position.

FIG. 3b shows the opposing needles 310, 320 in a closed position. The bodies 330 of the needles have been drawn together with a suitable force. The electrical conductive material 360 of each needle is also drawn together. An electrical energy supplied to the conductive material 360 by the generator (not shown) heats the conductive material 360, which in turn seals the dermis and sub-dermal layers of a wound.

In an alternative embodiment, FIG. 4a shows a device for energizing needles for wound healing. A needle holder and clamping mechanism 400 comprises a housing 410, opposing needle sets 450 and grasper mechanism 460. The housing 410 has a control 420 and an actuator 430 at a proximal end of the housing 410. The housing also has a generator connection 440 operable for supplying energy to the needles. At the distal end of the housing 410 is the set of opposing needles 450 and a grasper mechanism 460. The grasper mechanism 460 has two opposing elements. Together, the opposing elements of the grasper mechanism 460 operate to apply mechanical force to the needles 450.

In one embodiment of the invention, a user operates the needle holder and clamping mechanism to clamp a set of energized needles 450. The actuation mechanism 430 is operable to cause the grasper mechanism 460 to clamp inward and apply a mechanical force to the opposing needle sets 450. The grasper mechanism 460 is aligned in a manner that allows it to contact the opposing needles 450 and cause a clamping effect on the needles. As discussed above, the clamping effect of the needles causes the seal plates (not shown in FIG. 4a) to move from a first position to a closer second position, at a predetermined distance, thus causing a sealing surface between the needle sets 450. The opposing needles 450 are connected to an energy source via the generator connection 440. The control 420 provides user stabilization and also provides the user with a mechanism for altering the settings of the needle holder and clamping mechanism 400.

Figure 4B:
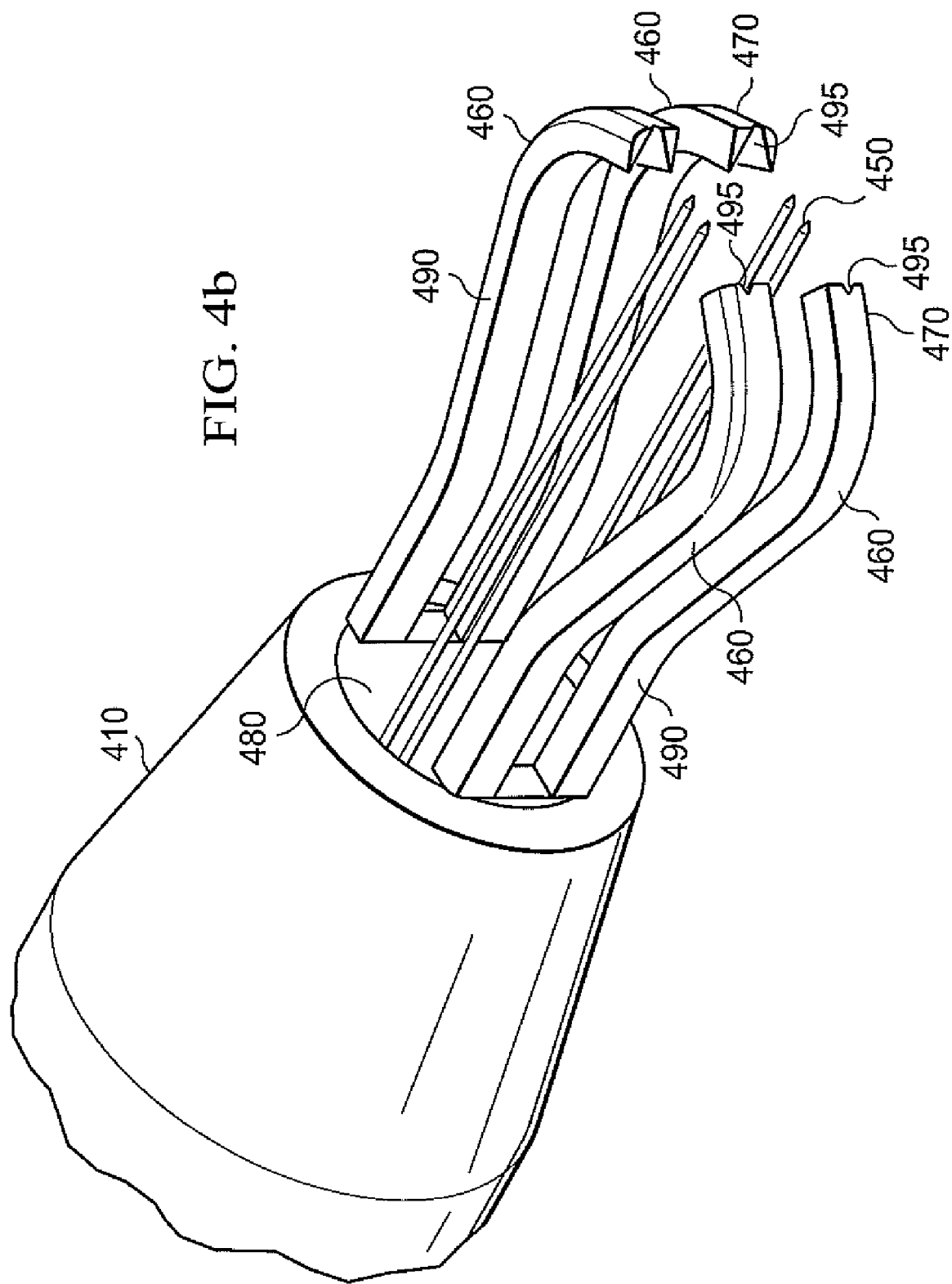

FIG. 4b is an enlarged view of the distal end of the needle holder and clamping mechanism 400. The housing 410 is further comprised of an opening 480. The opening 480 allows the opposing needles 450 and the grasper mechanism 460 to protrude from the housing 410. Each of the plurality of grasper mechanisms 460 is comprised of a grasper body 490 and a grasper tip 470. The grasper tip 470 is operable to grasp the opposing needle sets 450 in a manner that eliminates or lessens slippage of the opposing needle sets 450. The grasper tip 470 is formed with a grooved portion 495 that aligns with and holds the needles of the opposing needles 450. The grooved portion eliminates or substantially lessens potential movement of the opposing needles 450 allowing for precise insertion and usage of the opposing needles 450 for wound sealing purposes.

In the embodiment shown, the grasper mechanism 460 comprises a plurality of grasper bodies 490 and tips 470—there being a mechanism 460 associated with each of the needles in the opposing needles 450. Alternately, the grasper mechanism is a single bodied device comprising a single body on each side of the opposing needles 450 with a plurality of grooves in the tip to align with and hold the needles of the opposing needles 450. In another alternative, the opposing needles 450 and the grasper mechanism 460 are integrated. Accordingly, the needles 450 extend through the grasper mechanism 460 so that they protrude from the distal end of the grasper 460 and are connected internal to the housing 410 to an energy source via generator connection 440.

In the embodiment shown in FIG. 4a, the actuator 430 is used to control the depth of the penetration into the tissue of a patient and the clamping force of the opposing needles 450 when in the clamped position. The actuator 430 controls the clamping force by providing a feedback system to the user. In one embodiment, the feedback system is manual and the user determines the amount of force being applied to the clamping mechanism by feel. Alternatively, the feedback system is electronic. A sensor (not shown) is attached to the inside of the housing 410. The sensor provides an output (not shown) that is readable to a user. In one embodiment, the output is a simple numerical output that indicates a measure of pressure being applied.

The embodiment shown in FIGS. 4a and 4b functions to apply a mechanical force to the grasper mechanism 460 and energy to the needles. The needles 450 are inserted on opposing sides of a wound (not shown). The needles 450 are energized by an energy source via generator connection 440. It is understood that the energizing of the needles can occur prior to, during, or after insertion of the needles 450 into the skin. The mechanical force compels the graspers 460 inward. The graspers contact the opposing needles 450 and compel the needles 450 inward. The inward inducement of the needles 450 closes the wound. The amount of force used to mechanically close the graspers 460 and needles is variable depending on the wound and surrounding tissue characteristics.

The actuator 430 is utilized by a user to variably apply the force to the graspers 460 and needles 450. In an embodiment, the force is applied to the graspers 460 and needles 450 when the user pulls the actuator 430 out of the housing 410. In an alternate embodiment, the mechanical force is applied by the user with a twisting or clockwise, or counterclockwise, rotation of the actuator 430. It is understood by those skilled in the art that there are numerous possible manners to apply a force to the graspers 460 and needles.

In use, the user positions the needles to engage the opposing epidermis and dermis sections on opposing sides of a wound with each other. The opposing seal surfaces 370 (FIGS. 3a and b) of the needles 450 come together in aligned opposition due to the alignment action of the graspers 460. Other alternative embodiments will provide alternate alignment actions. An electrosurgical generator (not shown) is connected to the bipolar sealing instrument 400 through generator connection 440 on the housing 410. An electrical switch is used to close a circuit between the generator and the bipolar sealing instrument 400.

In an embodiment, the switch may be a footswitch, such as Valleylab's catalog number E6009, available from Valleylab Inc., Boulder Colo. The electrosurgical current flows through an electrically conductive path on each of the connector sets 50, 60 (FIG. 1), 250, 260 (FIG. 2) and the respective opposing sets of seal surfaces 370 (FIGS. 3a and b). An electrically insulating coating substantially covers each set of connectors 50, 60 (FIG. 1), 250, 260 (FIG. 2) and needles 450.

The outer surface of the needles 450 and graspers 460 may include a nickel-based material, a coating, a stamping, or a metal injection molding which is designed to reduce adhesion between the opposing needles 450 with the surrounding tissue during activation and sealing. Other components such as the housing 410 may be coated with the same or a different "non-stick" material. The materials are of a class of materials that provide a smooth surface to prevent mechanical adhesions.

It is also contemplated that the sealing surfaces 370 (FIGS. 3a and b) of the needles 450 may be manufactured from such "non-stick"materials as a nickel-chrome, a chromium nitride, a Med Coat 2000 manufactured by Electrolizing Corporation of Ohio, Inconel 600, tin-nickel, or any alloys thereof. High nickel chrome alloys and Ni200, Ni201 (about 100% Ni) may be made into sealing surfaces 370 by metal injection molding, stamping, machining or any like process.

These materials have an optimal surface energy for eliminating sticking due in part to surface texture and susceptibility to surface breakdown due to electrical effects and corrosion in the presence of biologic tissues. These materials exhibit good nonstick qualities and can be used on the sealing instrument 400 in areas where the exposure to pressure and RF energy can create localized "hot spots" more susceptible to epidermis adhesion. Reducing the amount of skin that "sticks" during sealing improves the overall efficacy of the instrument. The sealing surfaces 370 may also be coated with one or more of the above materials to achieve the same result. For example, Nitride coatings (or one or more of the other above-identified materials) may be deposited as a coating on another base material (metal or nonmetal) using a vapor deposition manufacturing technique.

The closed wound is held in the closed position during the sealing process. Effective sealing pressures may vary depending on the amount of tissue required to be grasped by the needles 450. Naturally, the amount of tissue will likewise depend on the nature and depth and width of a wound.

Figure 5:
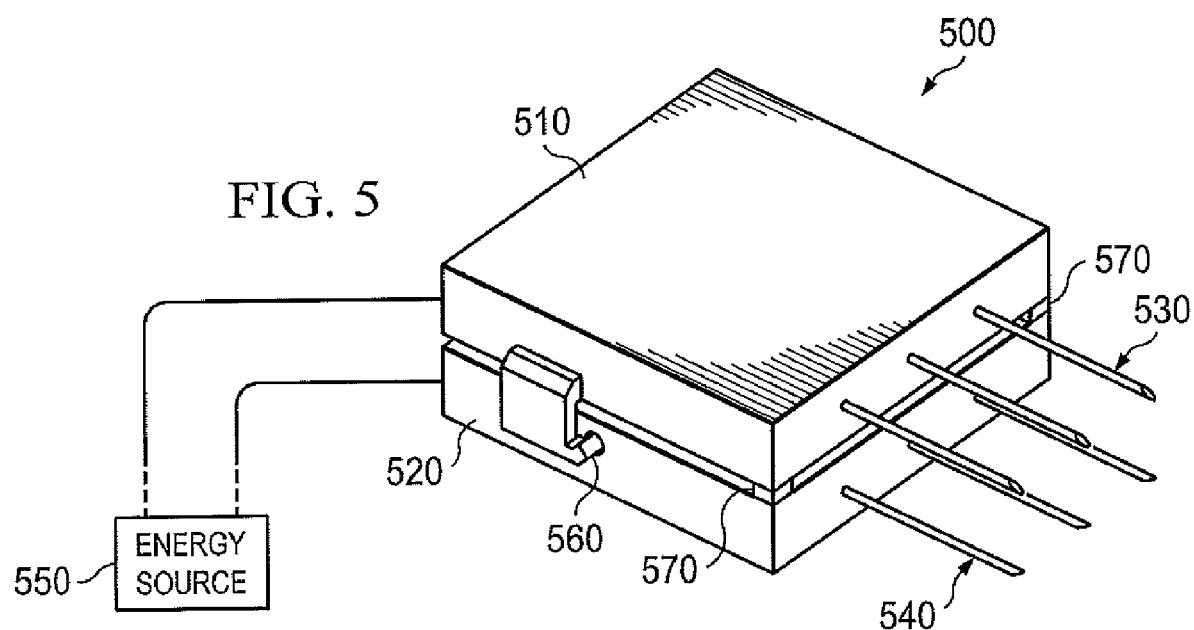
FIG. 5 is a view of an embodiment of a needle holder.

It is recognized that numerous varieties of clamping mechanisms and needle holding devices are possible. FIG. 5 shows an embodiment of a needle holder 500. The needle holder 500 comprises an upper structure 510 and a lower structure 520. A plurality of needles 530 are embedded in the upper structure 510. A plurality of needles 540 are embedded in the lower structure 520. The upper needles 530 and lower needles 540 oppose each other and form opposing sets of needles for wound sealing purposes. The opposing sets of needles 530, 540 are connected to an energy source 550. The connection between the energy source 550 and the needle sets 530, 540 runs through the upper and lower structures 510, 520. The needle holder 500 further comprises a pivot 560. The pivot 560 provides operable rotation of the upper and lower structures 510, 520 allowing for clamping and releasing. In this embodiment, mechanical stops 570 are provided. The mechanical stops 570 provide a limiting function. The upper and lower structures 510, 520 are not capable of rotating beyond the point where the stops 570 block further movement in the clamping direction. Accordingly, the stops 570 provide a minimum spacing between the needles sets 530, 540 when fully closed.

It is understood that there are several variations to the embodiment shown in FIG. 5. For example, the number of needles in each of the needle sets 530, 540 is variable. The number of needles can range from one to many. Also, the spacing of the needles is variable. Moreover, in one embodiment, the needle holder 500 is fully replaceable. It is envisioned that the holder 500 is a plug and play type device. The holder 500 operates much like a socket device. A portable set of holders 500 are insertable into the distal end of the housing (not shown in FIG. 5). The housing is equipped to accept a plurality of holders 500. Each different holder 500 is provided with a variable number of needles in each upper and lower set 530, 540. Also, alternatively each different holder 500 is provided with a variable number of needles in each needle set 530, 540 and a variable spacing of each the needles in each set. The housing is provided so that when a new holder is inserted into the housing, the connection to the energy source is automatically connected. One skilled in the art will fully understand the variety of manners in which a holder 500 will insert into the housing.

Figure 6:
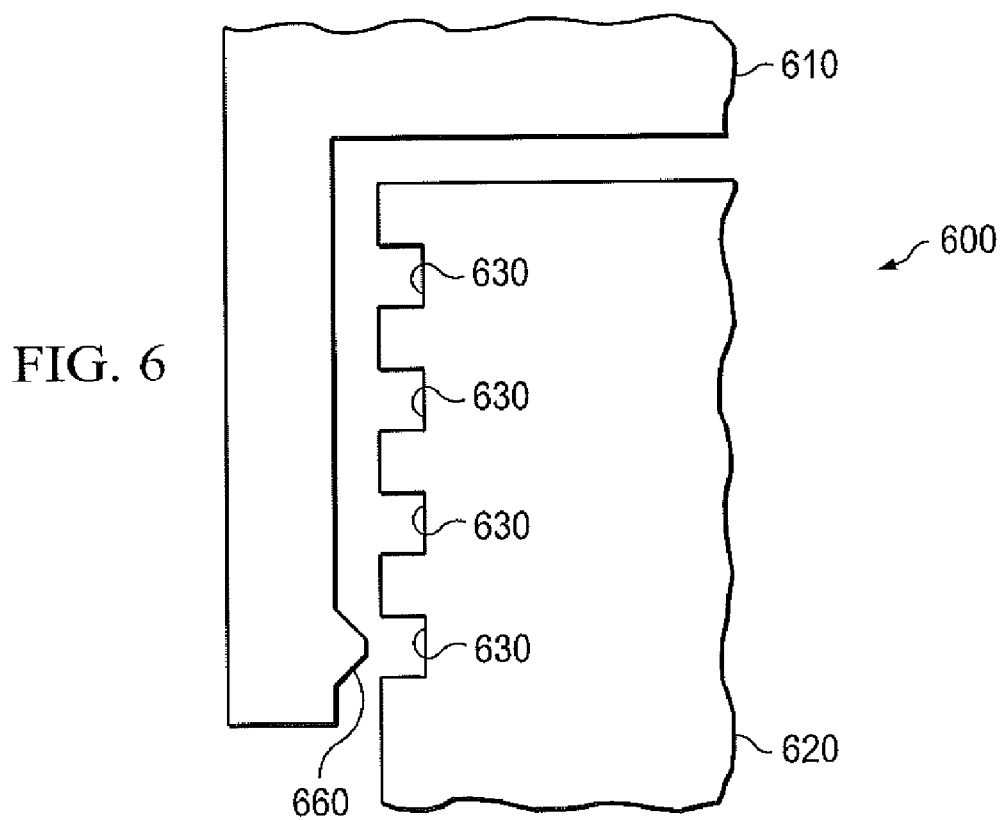
FIG. 6 is a view of an embodiment of a needle holder.

FIG. 6 shows an alternative embodiment of the needle holder of FIG. 5. The holder 600 comprises an upper structure 610 and a lower structure 620. The ends of the structures 610, 620 are not shown. The lower structure 620 has a plurality of latch positions 630. The pivot 660 is moveable into any one of the plurality of latch positions 630. The different latch positions 630 provide variable vertical spacing. Depending on the latch position 630 chosen for a particular wound, the required mechanical force will likewise vary.

It is understood that the embodiments of holders 500, 600 shown in FIGS. 5 and 6 are alternatives to the grasper 460 and needles 450 arrangements of FIGS. 4a and 4b. Rather than the grasper 460 of FIG. 4a engaging the needles 450 to induce them inward, the holder 500, 600 of FIGS. 5 and 6 firmly hold the needles and the needles are induced inward in like manner when the holder is forced to a closed position.

Figure 7A:
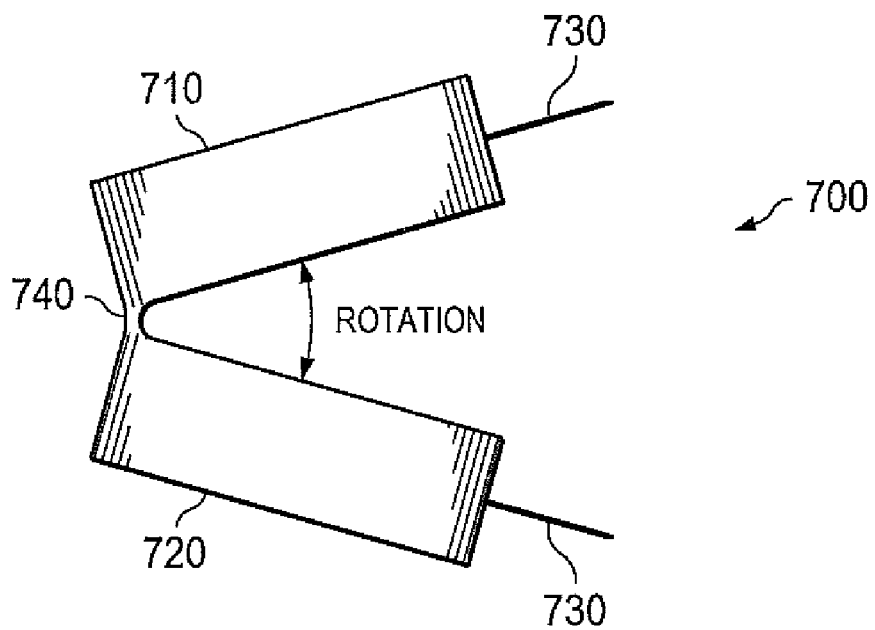
FIGS. 7a and 7b are views of embodiments of a needle holder.
Figure 7B:
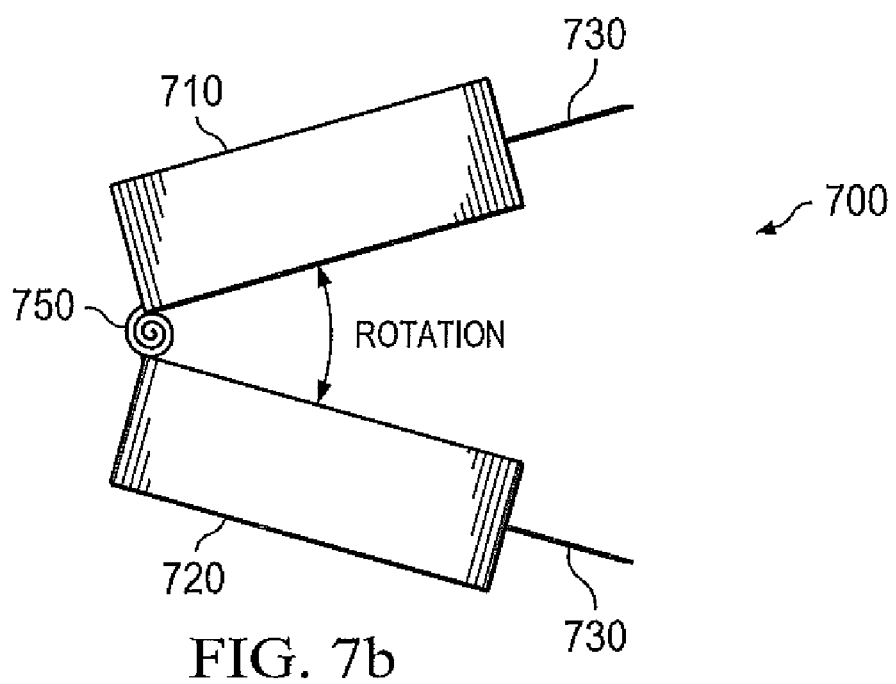

FIGS. 7a and 7b show alternative embodiments of a needle holder 700. The needle holder 700 has an upper structure 710 and a lower structure 720. Opposing needles 730 are embedded in the upper 710 and lower 720 structures. It is understood that the needles are connected to an energy source (not shown). The alternative in FIG. 7a provides a rotation mechanism 740 that allows the upper 710 and lower 720 structures to close together. The mechanism 740 is a hinge connecting the upper 710 and lower 720 structures. The hinge 740 is a pliable, or bendable, material. The hinge 740 has a natural state which is open. Accordingly, the hinge will return to its natural state, open, when a closing force is removed from the holder 700. This natural opening will assist in parting of the needles 730.

FIG. 7b shows an alternative embodiment. A torsion spring 750 is provided. The torsion spring connects the upper 710 and lower 720 structures. Similarly to the hinge 740, the hinge operates to force the upper 710 and lower 720 structures open when a closing force is removed.

Figure 8A:
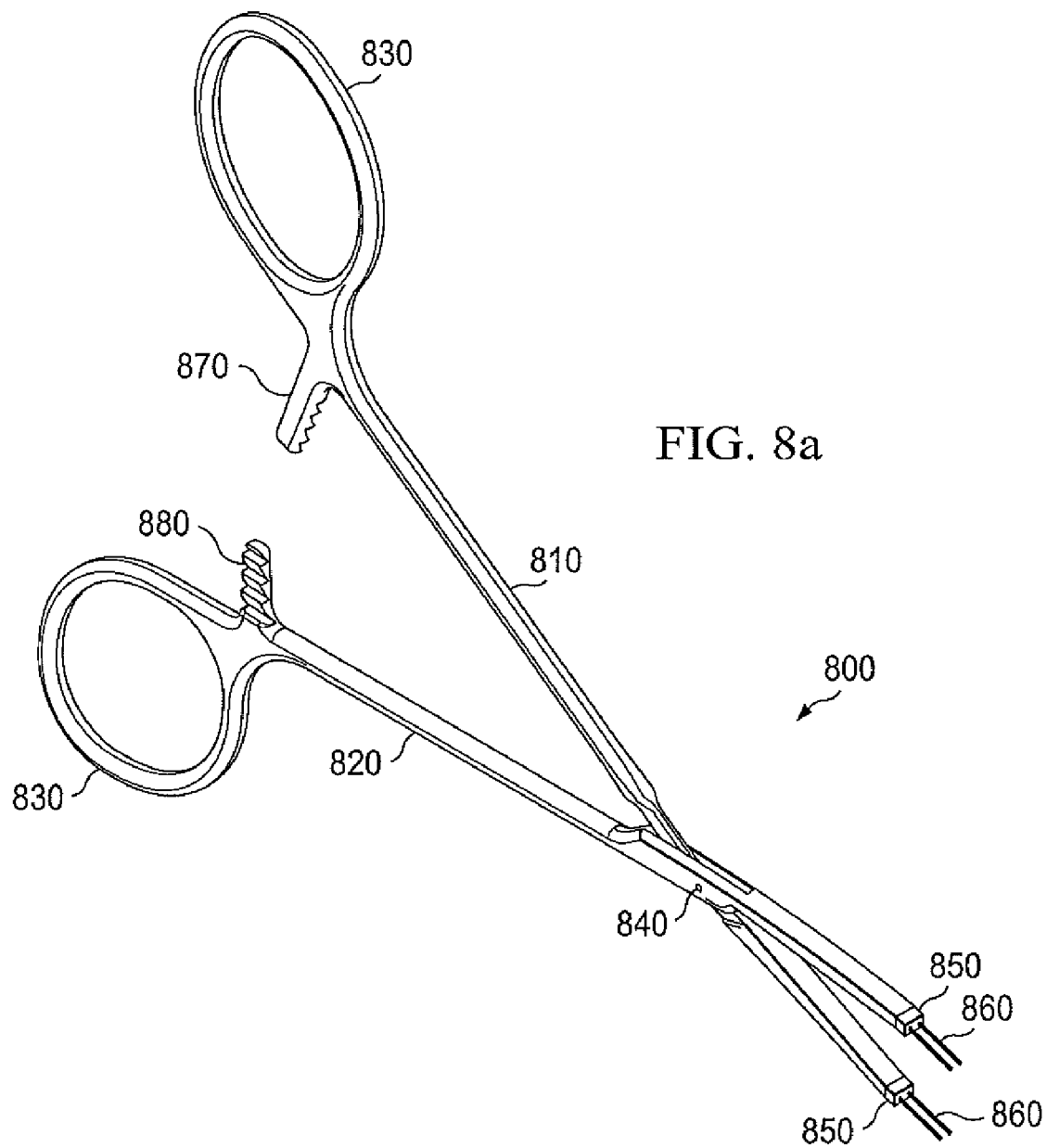
FIGS. 8a and 8b are views of embodiments of a needle holder and clamping mechanism.

FIG. 8a shows a needle holder and clamping mechanism 800. The hemostat styled holder 800 has an upper 810 and a lower 820 levering mechanism. At the proximal end of the levering mechanism 810, 820 are handles 830. The handles are configured to provide a gripping mechanism to a user (not shown). The levering mechanisms 810, 820 are connected at a pivot 840 toward the distal end. At the distal end of the mechanism 800, each mechanism 810, 820 has a needle holder 850. The needle holders hold a set of opposing needles 860. A mechanical force is applied to the needle holders 850 and needles 860 by drawing the handles 830 together. The handles further comprise a locking mechanism which has a clip 880 and a clip latch 870. The clip latch 870 has one or more locking position to provide variable positions for variable applications of force.

In an embodiment, the holders 850 are disposable pieces. The holders 850 are attachable and removable. The levering mechanisms 810, 820 are reusable. In an alternative embodiment, the holders 850 are incorporated into the hand piece.

Figure 8B:
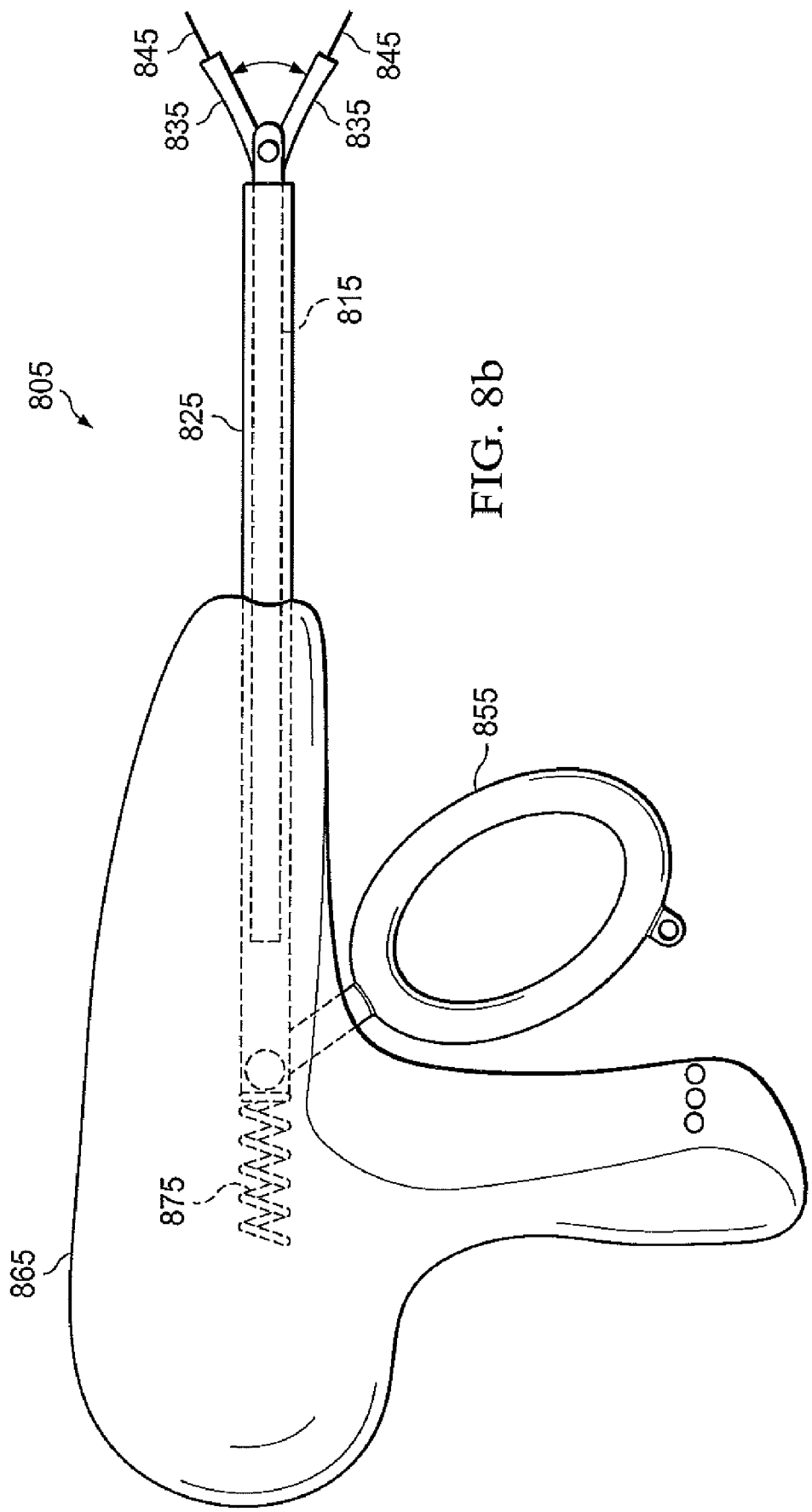

FIG. 8b shows an alternative needle holder and clamping mechanism 805. The shaft-based holder 805 has an inner 815 and outer shaft 825. At the distal end of the holder 805 and inner 815 and outer 825 shafts are a pair of opposed needle holders 835. Each holder 835 has a set of opposing needles 845. It is understood that there can be from one to a plurality of needles 845. The shafts 815, 825 are held at the proximal end of the mechanism 805 by a housing 865. The housing 865 provides a handle for a user. A lever mechanism 855 connected to the housing 865 is utilized by a user to operate the mechanism 805. The lever opens and closes the needle holders 835 by moving the inner shaft 815 relative to the other shaft 825. A spring 875 internal to the housing 865 applies clamping pressure to the holders 835 and needle sets 845.

Figure 9A:
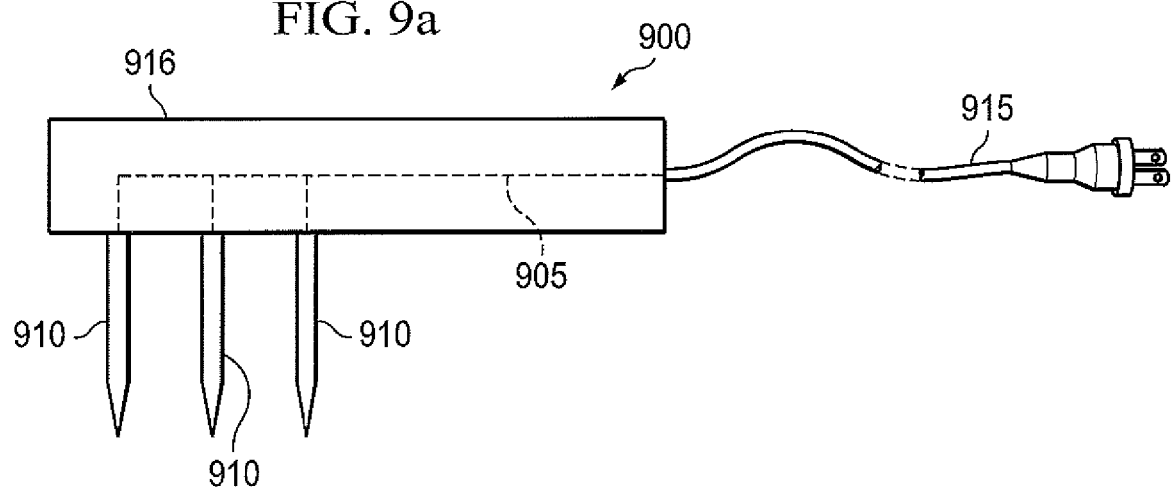

FIGS. 9a-d show embodiments of needle holders. FIG. 9a shows a needle holder 900 with an electrical connecting strip 905 connected to needles 910. The body 916 of the holder 900 is an electrically insulating material. Examples of electrically insulating materials are plastic and ceramic. The strip 905 is connected to all of the needles 910. It is understood that the needles 910 range in number from one to a plurality of needles. The connecting strip is connected to an energy source 915.

Figure 9B:
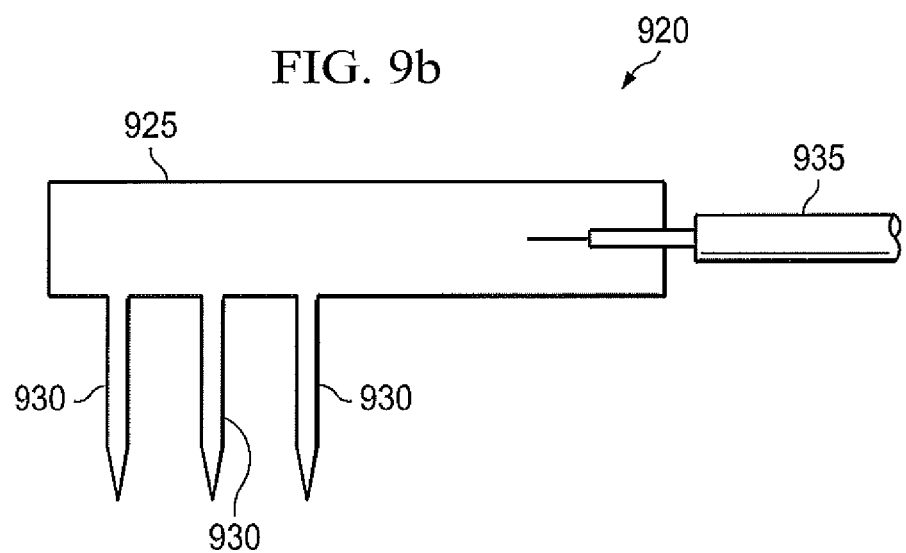

FIG. 9b shows a needle holder 920. A connecting strip 925 connects to needles 930. In this embodiment, the connecting strip 925 is integral to the needles 930. The strip 925 and needles 930 are a one piece design. The connecting strip is connected to an energy source 935. The energy source 935 is connected to the strip by a common methods such as crimping, welding or other method. The connecting strip 925 and needles 930 are a one piece construction. Those skilled in the art will recognize numerous methods to form a one piece construction. Such methods include stamped metal, metal injection molding or machining. It is understood that the needles 930 range in number from one to a plurality of needles.

FIG. 9c shows a needle holder 940. A connecting strip 945 connects to needles 950. In an embodiment, the needles 950 are attached to the strip. Those skilled in the art will recognize numerous methods of connecting the needles 950 to the strip 945. Examples include welding, press fitting or the strip could be formed to create the mechanical and electrical connection. It is understood that the needles 950 range in number from one to a plurality of needles. The connecting strip is connected to an energy source 955.

FIG. 9d shows a needle holder 960. A connecting strip 965 connects to needles 970. In an embodiment, the strip 965 is a die cast holder. The needles 970 are inserted into the die cast. The strip 965 connects to an energy source 975. The energy source is inserted into the die cast. It is understood that the needles 970 range in number from one to a plurality of needles.

Figure 10:
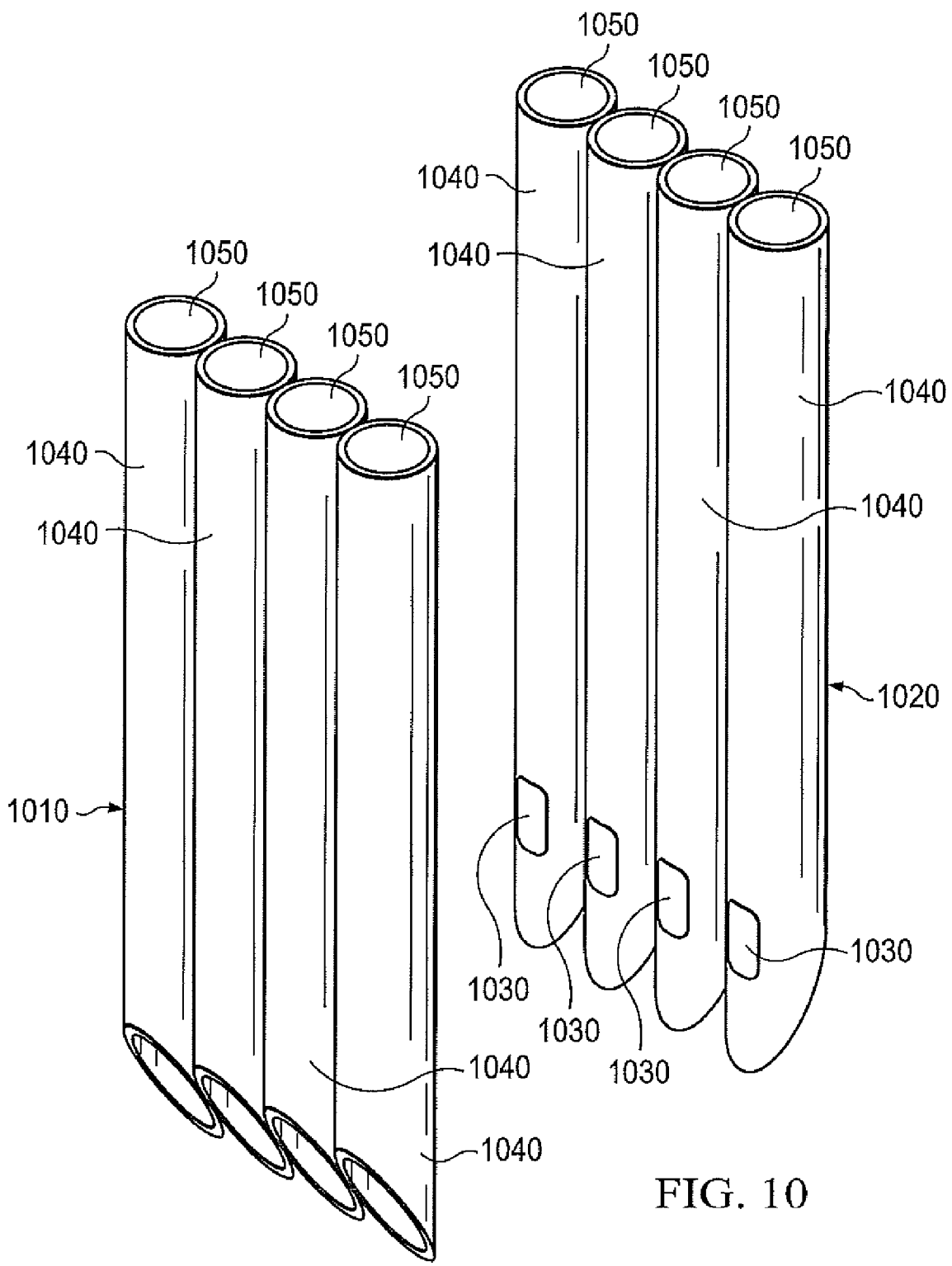
FIG. 10 is an embodiment of a needle configuration.

FIG. 10 shows an embodiment of a needle configuration. A first set of needles 1010 is opposed by a second set of needles 1020. In an embodiment, the needles 1040 are hollow. A hollow needle 1040 allows items and functional parts to be inserted through the needles 1040 to provide a connectivity between the distal portion of the needle tip, the proximal portion of the needle 1040 and any grasping mechanism or otherwise. A sealing plate 1030 is on each needle 1040 in each of the opposing needle sets 1010, 1020. An electrical connection 1050 connects the sealing plates 1030 to a power source (not shown).

As shown in FIG. 10, needles 1040 are adjacent each other in each respective opposing needle set 1010, 1020. In an embodiment, a mechanism (not shown) in a needle holder device brings the needles 1040 to an adjacent position as shown. The adjacent aspect of the needles provides an increase in the likelihood that opposing members (needles) 1040 in the opposing needle sets will meet up.

In an embodiment, the body of the needles 1040 are constructed of a ceramic or plastic insulator. In another aspect of the invention, the body of the needles 1040 are constructed of a non-insulative material. The non-insulative body of the needles 1040 is coated with an insulative material such as a ceramic or plastic. A non-conductive needle body 1040 or coating and seal plate 1030 allows for control of thermal phenomena. Those skilled in the art will recognize that there are many suitable materials to provide non-conductive properties to the needles 1040.

Figure 11:
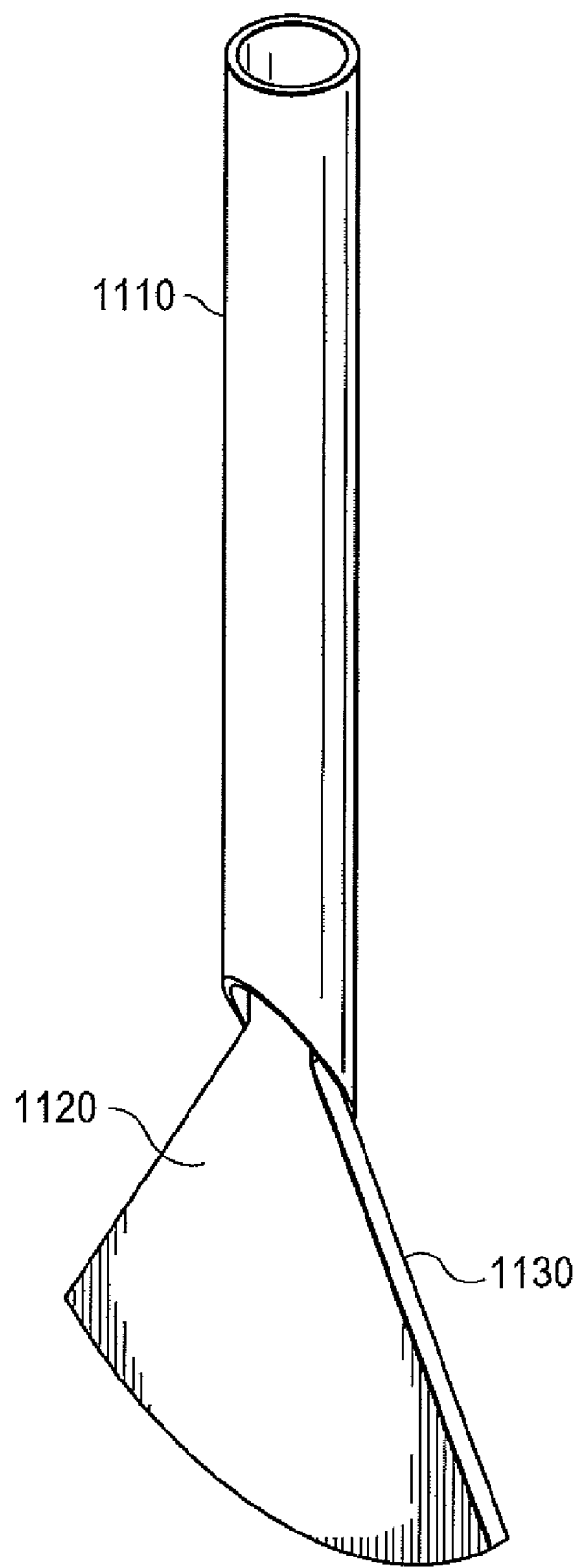
FIG. 11 is an embodiment of a needle configuration.

FIG. 11 shows an embodiment of a deployable needle configuration. A needle body 1110 is hollow. A hollow needle 1110 body allows items and functional parts to be inserted through the needles 1110 to provide a connectivity between the distal portion of the needle 1110 tip, the proximal portion of the needle 1110 and any grasping mechanism or otherwise. Prior to insertion and use, a deployable, fanlike mechanism 1120 resides inside the hollow needle 1110. The deployable mechanism 1120 expands as it is deployed outward from the distal end of the needle 1110.

In an embodiment of the invention, the deployable mechanism 1120 is fanned. The fanned aspect of the deployable mechanism 1120 allows the mechanism 1120 to fit inside the hollow needle 1110 prior to deployment. In an embodiment, the deployable mechanism 1120 is constructed of a conductive material thereby allowing the mechanism 1120 to act as a sealing plate. To avoid energy loss, an insulative material is provided on the back side 1130 of the mechanism 1120. In an embodiment, the insulative material is a ceramic or plastic coating. In an alternative embodiment, the insulative material is a second fanlike mechanism (not shown). Those skilled in the art will recognize that there are many suitable materials to provide non-conductive properties to the needles 1110. For instance, Alumina or Zirconia are particularly suitable as non-conductive, insulative materials that provide sufficient flexibility and resilience to act as a fanlike member for the mechanism or as a coating.

In operation, the needle 1110 is inserted into a patient's skin. It is understood that there is an opposing needle, or needle set, (not shown) to provide opposing sealing plates. The mechanism 1120 is then induced outward from the hollow needle 1110 to create a sealing plate. The inducing device (not shown) can range from any of a multitude of well known devices for providing force.

Figure 12:
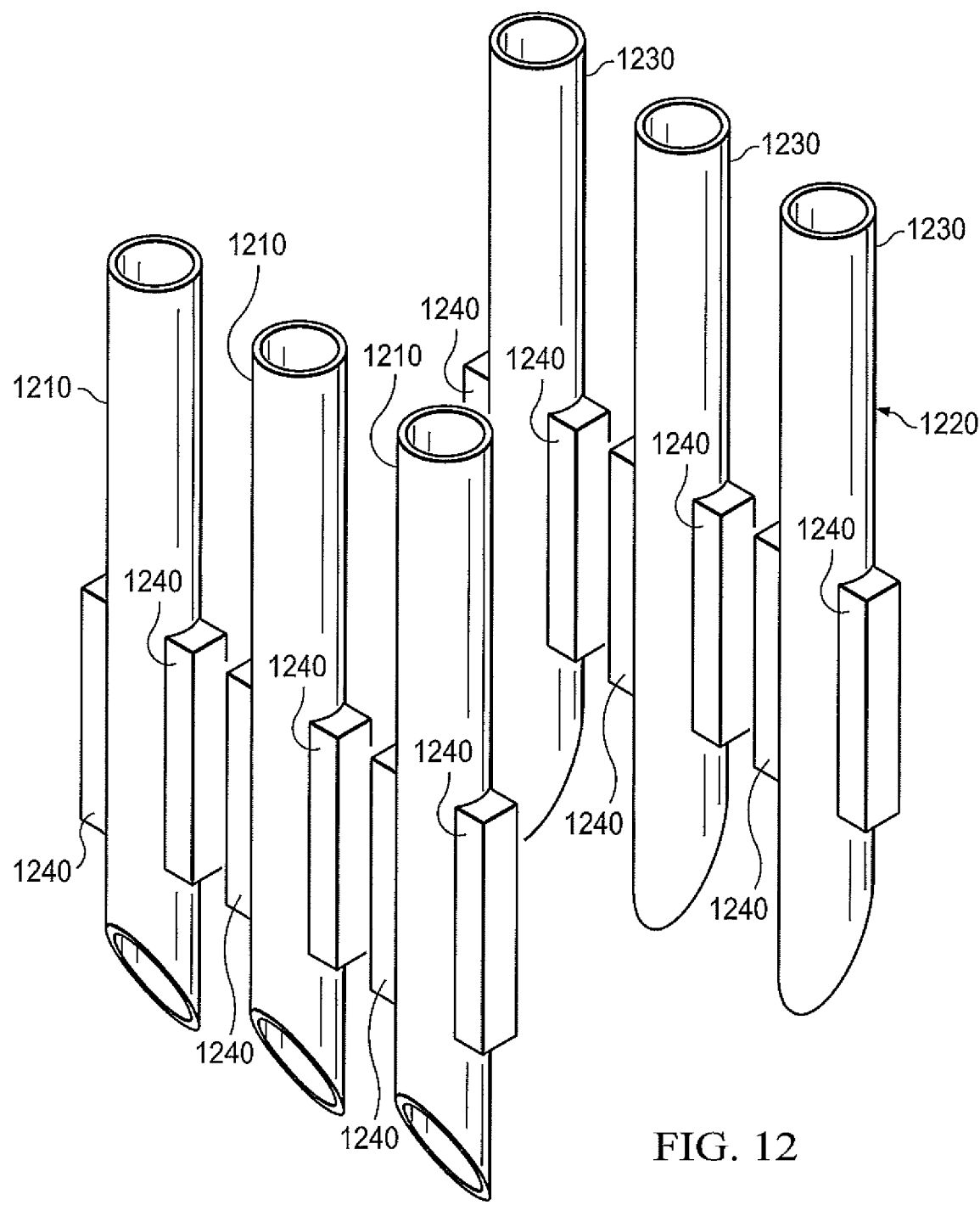
FIG. 12 is an embodiment of a needle configuration.

FIG. 12 shows an embodiment of a needle configuration. A first set of needles 1210 is opposed by a second set of needles 1220. A hollow needle body 1230 of each needle allows items and functional parts to be inserted through the needles 1210, 1220 to provide a connectivity between the distal portion of the hollow needle body 1230, the proximal portion of the needle body 1230 and any grasping mechanism or otherwise. Retractable seal plates 1240 reside inside each hollow needle body 1230. Prior to insertion and use the retractable seal plates 1240 extend from inside the needle body 1230. The extended retractable seal plates 1240 increase the seal area of each needle and increase the likelihood that opposing seal plates will meet up to cause a seal.

In an embodiment, the needle bodies 1230 are constructed of a ceramic or plastic insulator. In another aspect of the invention, the body of the needles 1230 is constructed of a non-insulative material. The non-insulative body of the needles 1230 is coated with an insulative material such as a ceramic or plastic. A non-conductive needle body 1230 or non-conductive coating in conjunction with a conductive seal plate 1240 allows for control of thermal phenomena. Those skilled in the art will recognize that there are many suitable materials to provide non-conductive properties to the needles 1230.

In an embodiment, an insulative material is provided on the back side of the retractable seal plates 1240. The insulative material on the back side is useful to avoid energy loss.

In operation, the needles 1210, 1220 are inserted into a patient's skin. The retractable seal plates 1240 are induced to extend out of the needle bodies 1230 to expose the sealing plates. The inducing device (not shown) can range from any of a multitude of well known devices for providing inducing extension in a device.

FIGS. 13a and 13b shows an embodiment of a needle configuration. A needle body 1310 is hollow. The hollow needle 1310 body allows items and functional parts to be inserted through the needles 1310 to provide a connectivity between the distal portion of the needle 1310 tip, the proximal portion of the needle 1310 and any grasping mechanism or otherwise. Prior to, or after, insertion, deployable flaps 1320 rotate outward from the body of the needle 1310. The flaps 1320 are part of the needle body 1310 and maintain their connection to the body 1310 at a pivot point 1330. The flaps 1320 operate to catch opposing needles 1310 in order to maintain proximity.

In an embodiment, the needle bodies 1310 and flaps 1320 are constructed of a pliable insulator. A plastic is suitable for providing sufficient pliability and resilience to avoid breakage of the flaps. A mechanism internal to the needle bodies 1310 provides force for inducing the flaps 1320 to extend. It is understood by those skilled in the art that there are many suitable materials to provide non-conductive properties to the needles 1310 and flaps 1320.

In operation, the needles 1310 are inserted into a patient's skin. The flaps 1320 are induced to extend outward from the needle body 1310. The inducing device (not shown) can range from any of a multitude of well known devices for inducing extension in a device.

It is to be understood that the above described embodiments are only illustrative of the application of the principles of the present disclosure. Numerous modifications and alternative arrangements may be devised by those skilled in the art without departing from the spirit and scope of the present disclosure. The appended claims are intended to cover such modifications and arrangements.

What is claimed is:

1. An electrosurgical instrument, comprising:
    a first penetrating component, comprising a first set of needles, a second penetrating component comprising a second set of needles, a first connector connected to the first penetrating component, and a second connector connected to the second penetrating component;
    wherein each needle of the first and second penetrating components comprises; a body portion and a sealing surface;
    a hinge pivotally joining the body portions of the first penetrating component and the body portions of the second penetrating component, wherein
    each of the first and second set of needles extends from the respective first and second connector in substantial radial alignment with the hinge axis;
    the first and second connectors are adapted to connect to an electrical energy source such that the sealing surfaces are capable of conducting bipolar energy therebetween; and
    the first and second penetrating components are pivotable about the hinge from a first position wherein the first and second components are disposed in spaced opposing relation relative to one another, to a second position wherein the first and second penetrating components are closer to one another than in the first position.

2. An electrosurgical instrument according to claim 1, wherein the body portions of the first and second penetrating components are made of an electrically insulating material and wherein the sealing surfaces are coated with an adhesion reducing material.

3. An electrosurgical instrument according to claim 1, wherein the first and second connectors are embedded in a manually manipulable covering, the covering having a first and second side wherein the first and second sides are opposed to each other and connect at a pivot point.

4. The electrosurgical instrument according to claim 3, wherein:
    the body portions of the penetrating components is made of an electrically insulating material; and
    the sealing surfaces are coated with an adhesion reducing material.

* * * * *